United States Patent [19]

Kothe

[11] Patent Number: 5,045,053

[45] Date of Patent: Sep. 3, 1991

[54] DEVICE FOR RECOVERING A TISSUE SAMPLE OR TISSUE FLUID

[76] Inventor: Lutz Kothe, Bodmaner Str. 15, D07764 Radolfzell 14, Fed. Rep. of Germany

[21] Appl. No.: 369,304

[22] Filed: Jun. 21, 1989

[30] Foreign Application Priority Data

Jun. 24, 1988 [DE] Fed. Rep. of Germany ....... 3821336
Apr. 14, 1989 [DE] Fed. Rep. of Germany ....... 3912257

[51] Int. Cl.$^5$ .............................................. A61N 1/30
[52] U.S. Cl. ....................................... 604/21; 604/30; 604/32; 604/35; 604/248
[58] Field of Search ...................... 604/248, 19, 21, 30, 604/32, 35, 246, 319

[56] References Cited

U.S. PATENT DOCUMENTS

| 3,680,560 | 8/1972 | Pannier, Jr. et al. | 604/320 |
| 4,296,748 | 10/1981 | Kurtz et al. | 604/319 X |
| 4,447,226 | 5/1984 | Mayoral | 604/32 X |
| 4,950,230 | 8/1990 | Kendall | 604/248 X |

Primary Examiner—Robert Bahr
Assistant Examiner—J. L. Doyle
Attorney, Agent, or Firm—Bachman & LaPointe

[57] ABSTRACT

In a device for the recovery of a tissue sample, tissue fluid or similar, which is detached and/or aspirated by a surgical instrument, tubing is provided between the surgical instrument and a collecting device. A vacuum-producing apparatus is assigned to the tubing. In this case the tubing (5) is to be connected to a transmission head (4), which rests with a ring seal (15) on the collecting apparatus (7).

23 Claims, 6 Drawing Sheets

DEVICE FOR RECOVERING A TISSUE SAMPLE OR TISSUE FLUID

BACKGROUND OF THE INVENTION

The present invention relates to a device for recovering a tissue sample, tissue fluid or the like, which is detached and/or aspirated by a surgical instrument comprising tubing being provided between the surgical instrument and a collecting device, to which tubing a vacuum-producing apparatus is attached.

U.S. Pat. No. 4,881,550 describes a medical device having an apparatus containing cutting forceps for the extraction of tissue samples, removal of elongated parts of the body, such as sections of nerves or veins, or the like, wherein an inner tube is inserted into an outer tube. The relative movement between the inner tube and the outer tube operates an apparatus containing cutting forceps, by which corresponding tissue samples are cut off. Said medical device is connected via corresponding tubing to a collecting apparatus and the extracted tissue samples are aspirated by the creation of a vacuum.

The object of the present invention is to circumscribe in more detail a device for recovering a tissue sample, tissue fluid or the like, which is economical to manufacture and simple to operate.

SUMMARY OF THE INVENTION

The foregoing object is achieved by the present invention wherein tubing is connected to a transmission head, which is seated on the collecting apparatus with a ring seal.

By way of the present invention, the actual surgical instrument is separated from the device for recovering the samples. In practice it has been shown that it is not favorable for the surgical instrument or the tubing to be permanently attached to the collecting apparatus, as the vacuum causes not only desired tissue samples but also tissue fluid, for example, to be aspirated. In order to separate desired and undesired extracted material the invention provides for the transmission head to be connected to a rotary valve unit.

By means of the rotary valve unit it is possible to establish and break the connection between the transmission head and the vacuum-producing apparatus.

A number of embodiments of the rotary valve unit are conceivable and are covered by the present invention. The rotary valve unit preferably consists in a simple embodiment, of a base disk and a rotating disk connected to the transmission head, the rotating disk having an axis with respect to the base disk. The base disk in turn has a connection to a line leading to the vacuum pump. The rotating disk on the other hand has at least two boreholes, which can be connected alternatingly with the connection or with a borehole in the base disk. One of the boreholes is used to couple the transmission head with the vacuum pump, and with the other borehole a connection is created via tubing to a separate collecting container. This separate collecting container is used to collect undesired extraction material, for example tissue fluid. For this purpose the collecting container is in turn to be connected via tubing to the transmission head, depending on what operating position the transmission head is in.

The transmission head itself is, moreover, connected via a rotating lever to the rotary valve unit. Said rotating lever is penetrated by a longitudinal borehole which has on the one side a connection to the vacuum pump and on the other side opens into a chamber formed in the transmission head.

The chamber is penetrated partially by a sleeve which is in turn connected to the tubing leading to the surgical instrument.

The sleeve has a sleeve opening and is connected with said opening to a connection seal to the tubing to the collecting container.

It is thus possible in a simple manner to place the transmission head on the collecting apparatus in the case of a desired extraction, whereas it is to be connected to the collecting container in the case of an undesired extraction, a vacuum being created in both cases, the assignment of which to one of the two activities is effected solely by the rotary valve unit or turning of the transmission head respectively.

It should preferably be possible to ventilate the chamber in order for the vacuum to be released both when the transmission head is lifted off the collecting apparatus and by the connection to the collecting container. In this way desired or undesired extractions are prevented from taking place in this operating position.

In a preferred exemplary embodiment the chamber in the transmission head has for this purpose a borehole which can be closed by a lever. Using this lever the transmission head is raised so that the chamber is ventilated at the same time as lifting occurs.

In another exemplary embodiment of the invention the transmission head may consist of a principal housing surrounding an inner chamber, into which a connection nozzle for a vacuum line opens.

In order to ventilate this inner chamber boreholes or ventilation openings are provided in the housing, which can, for example, be closed via a sliding sleeve and a corresponding seal.

The connection between transmission head and tubing leading to the surgical instrument should be constructed in such a way that it can be easily released. This makes it easier when exchanging different surgical instruments or alternatively in the event that, for example, the tubing is blocked by a tissue sample. According to the invention, therefore, the tubing opens into a connection piece which engages in a locking manner with the transmission head. For the sake of simplicity the locking connection consists of a segmented ring sleeve at the transmission head the latter in itself forming a ball seat. A ball of, the connection piece can lock into this ball seat, in which case said ball is further provided with a ring seal in the direction of the inner chamber. If a vacuum is created in the inner chamber of the transmission head such a vacuum pulls the ball against the ring seal and presses both against the ball seat in the ring sleeve.

The inventor has also devised novel ideas for the collecting device. In the preferred exemplary embodiment the collecting device consists of a supporting body and a rotating plate placed upon the latter. In the supporting body a drive for the rotating plate is to be provided, such drive consisting, for example, of a stepping motor which can be pneumatically activated.

The position of the rotating plate or its attachment is determined by corresponding locking balls between the supporting body and the rotating plate. For the sake of simplicity said locking balls are spring-mounted.

The rotating plate itself in turn consists of a supporting plate and a covering disk, between which the collars of test tubes are clamped. In this case the supporting disk has corresponding push-through openings for the test tubes. It is self-evident that the supporting disk is constructed so that it can be detached from the covering disk and thus the test tubes can be removed.

The complete rotating plate should preferably be constructed so as to be detachable from the supporting body and for this purpose, for the sake of simplicity, it is placed on a drive shaft or similar.

The entire device is constructed as simply as possible and is therefore economical to manufacture. It is not subject to any wear whatsoever and can be moved in a simple manner with the aid of the rotatable transmission head from one operating position into another.

If required, all the movement processes can be made automatic or semi-automatic. For this purpose the inventor has also developed a device in which the corresponding collecting devices are arranged not in a circle but linearly. The collecting devices in this case would normally probably consist of magazines for test tubes or secretion bottles.

The magazines are arranged in a shaft of a housing to which a guide rail for a carriage bearing the transmission head is assigned. Corresponding sensors are used to control the positions of the transmission head and to assign them to the corresponding test tubes or secretion bottles.

The carriage bearing the transmission head is preferably motor driven, any mechanical construction being conceivable in this case.

Automation also includes it being possible for the inner chamber of the transmission head to be automatically ventilated. The abovementioned sliding sleeve in particular is especially suited for this purpose as it can be raised by an electromotor, causing the ventilation openings to the inner chamber to be exposed. Other constructions, however, are also conceivable in this case.

BRIEF DESCRIPTION OF THE DRAWINGS

Further advantages, features and details of the invention can be seen from the following description of preferred exemplary embodiments and from the drawing, in which

FIG. 6 shows a perspective view of a further embodiment of a device according to the invention for recovering tissue samples or similar;

DETAILED DESCRIPTION

Figure 1:
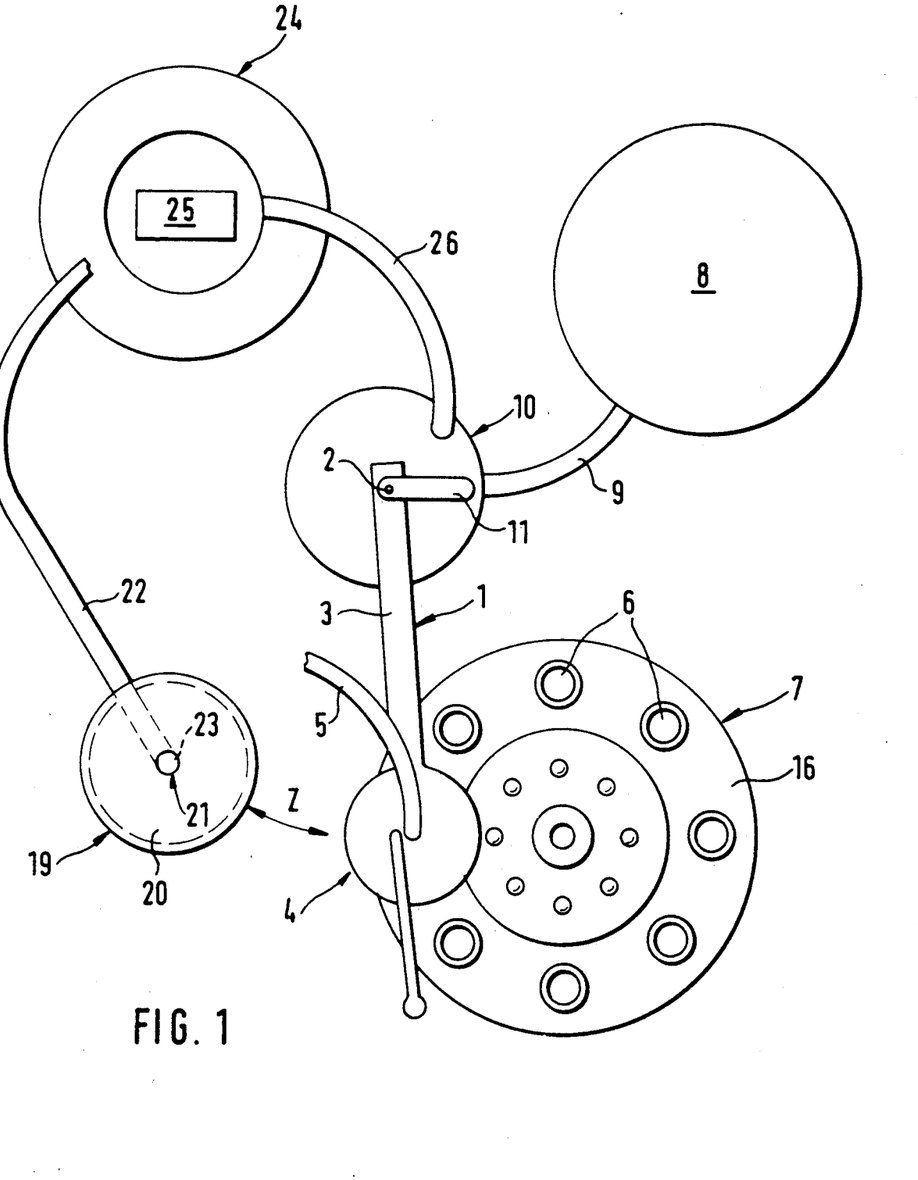
FIG. 1 shows a diagrammatically represented plan view of a device according to the invention for recovering tissue samples or similar, FIG. 2 shows a diagrammatically represented plan view of the device according to FIG. 1 in a further operating position.

A device according to the invention for the recovery of tissue samples or similar has, according to FIG. 1, a rotating arm 1, which is rotatable around a rotating axis 2 in the direction z. This rotating arm 1 consists essentially of a rotating lever 3 and a transmission head 4.

Tubing 5 which is connected to a corresponding apparatus containing cutting forceps (not shown in greater detail), as is disclosed, for example, in German Utility Model G 87 02 446, opens into the transmission head 4.

A tissue sample from the tubing 5 passes via this transmission head 4 into corresponding test tubes 6 of a collecting apparatus 7.

In order to draw off the tissue samples the rotating arm 1 has a connection to a corresponding vacuum pump 8. This connection is indicated by the line 9. This line 9 opens into a rotary valve unit 10, which is connected via a line piece 11 to the rotating arm 1.

Figure 2:
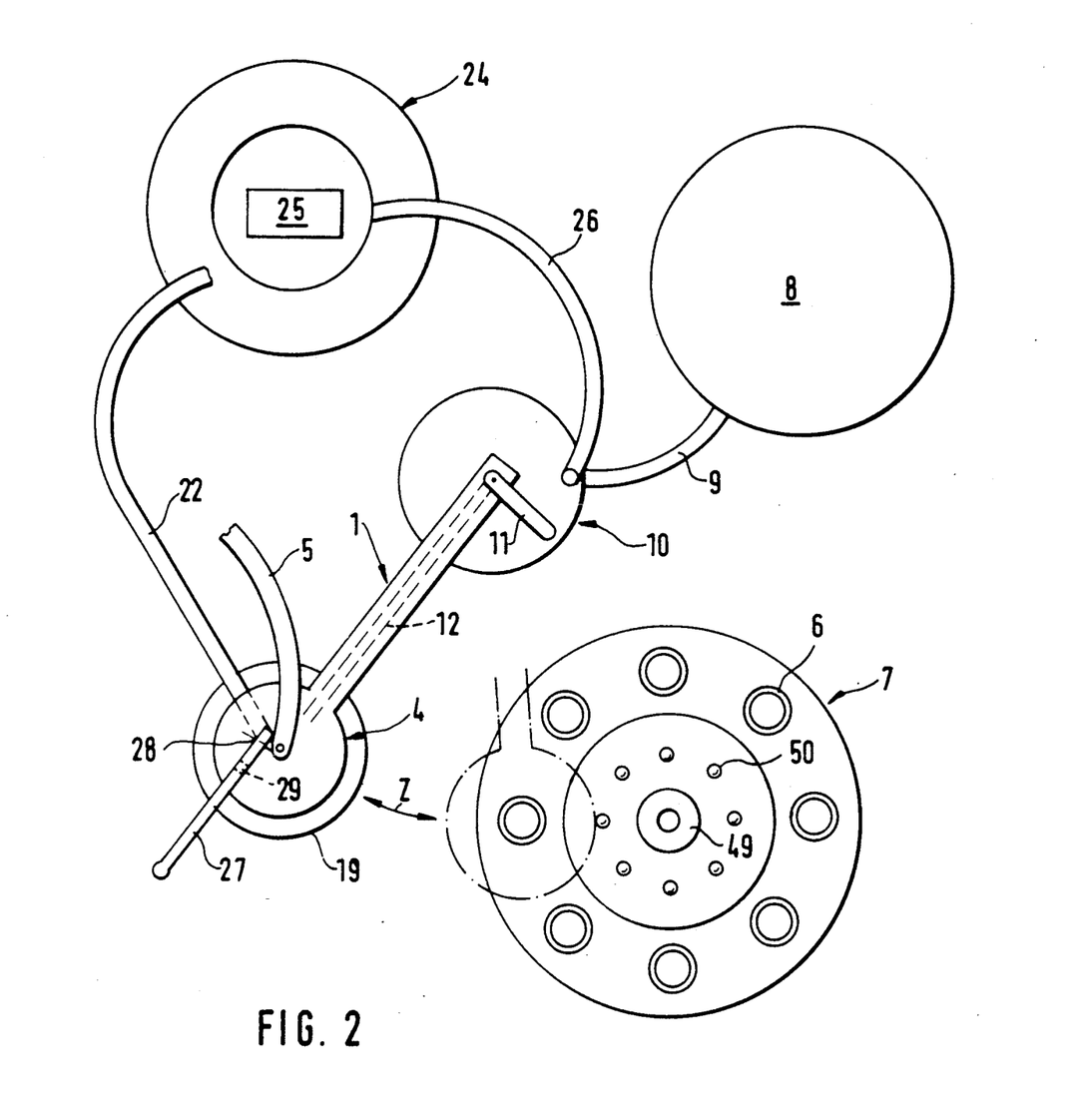
Figure 3:
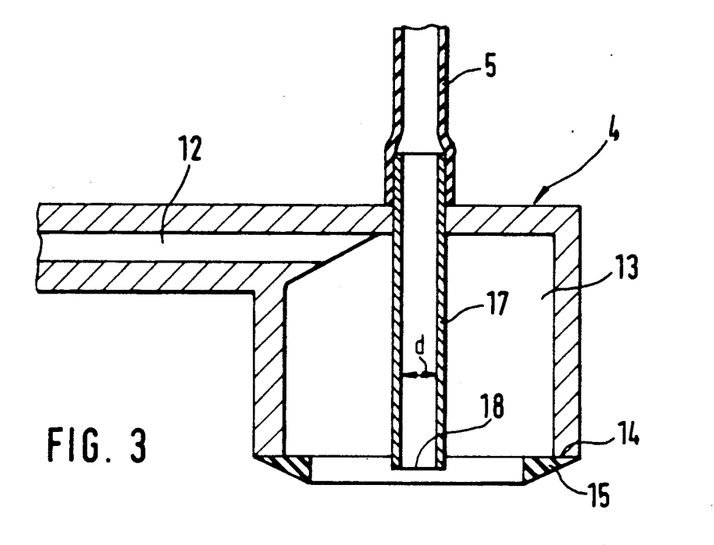
FIG. 3 shows an enlarged cross-section through a transmission head of the device according to FIGS. 1 and 2.

For this purpose the line piece 11 has a connection to a longitudinal borehole 12, shown by broken lines in FIG. 2, the borehole, as illustrated particularly in FIG. 3, opening out in a chamber 13 into the transmission head 4.

The circumferential edge 14 of the transmission head 4 is provided with a ring seal 15, which according to FIG. 1 rests on a disk 16 and thus encloses a test tube 6. In this operating position a vacuum can be created in the chamber 13 by means of the vacuum pump 8, so that tissue samples are aspirated by the tubing 5. The tubing 5 in this case is placed on a sleeve 17, which crosses through the major part of the chamber 13.

In this arrangement the vacuum is created in such a way that, given the relatively small diameter d of the sleeve 17 or of the tubing 5, it is sufficient to draw off the tissue sample, but that the latter can drop into the corresponding test tube 6 after emerging from the sleeve opening 18. As a result of the corresponding volume of the chamber 13 this vacuum is for the most part released when the tissue sample emerges from the sleeve opening 18.

In many applications it is desirable that, before the actual drawing off of tissue samples, for example, tissue fluid should be removed by suction or no vacuum should be created in conjunction with the filling of a test tube 6. For this purpose the rotating arm 1 is located in the operating position shown in FIG. 2. In this case the transmission head 4 rests on a container 19, which is closed with a lid 20. A connection fitting 21 passes through said lid 20, tubing 22 being pushed onto the connection fitting in the inside of the container 19. On the other side this connection fitting has a connection seal 23, which, in the operating position shown in FIG. 2, encloses the sleeve 17 in the region of the sleeve opening 18.

The tubing 22 leading from the container 19 opens into a further closed collecting container 24. In this collecting container 24 a pressure measuring instrument 25 is provided, by means of which the corresponding vacuum pressure can be determined. This pressure measuring instrument 25 is also connected via tubing 26 to the rotary valve unit 10.

In this arrangement, in the operating position shown in FIG. 2, a connection is established by means of this rotary unit 10 between the tubing 26 and the line 9 to the vacuum pump 8. In this way a vacuum is created in the collecting container 24, via which corresponding tissue fluid or similar is drawn off by the tubing 22 from the tubing 5. As a result of the fact that the sleeve 17 rests with its sleeve opening 18 directly on the connection seal 23, no drop in vacuum takes place in the transmission head 4, so that the fluid can be sucked into the collecting container 24 without interruption.

In order to turn the rotating arm 1 in the direction of rotation z a lever 27 is furthermore assigned to the transmission head 4. Together with the transmission head 4 this lever 27 forms a rotary joint 28, which is shown only by a dot-dash line in FIG. 2. In the operating position the lever 27 closes a borehole 29 which leads to the chamber 13. If the lever 27 is raised, the chamber 13 is also ventilated by means of this borehole 29 and the vacuum is equalized.

Figure 4:
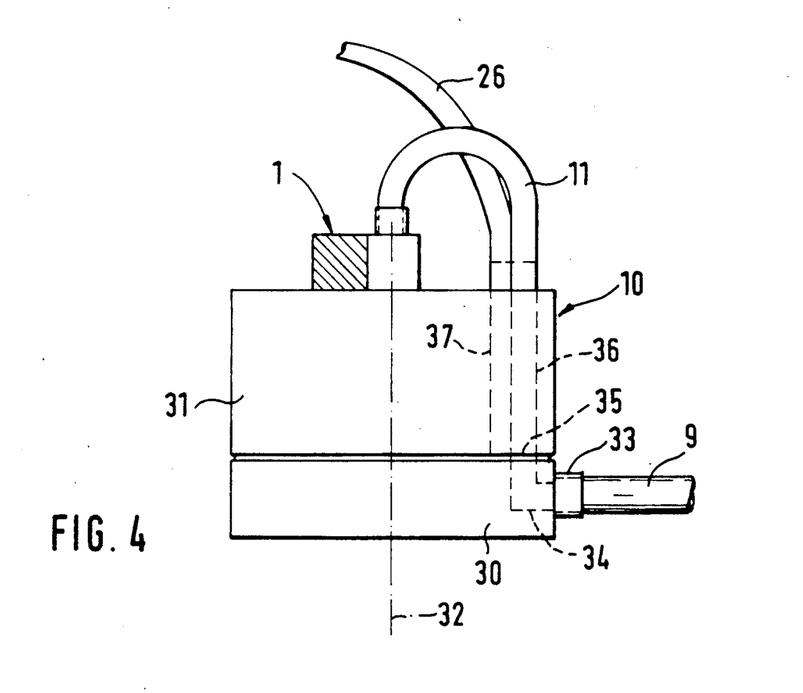
FIG. 4 shows a side view, broken in part, of a rotary valve unit.

The rotary valve unit 10 consists, for the sake of simplicity, of a base disk 30 and a rotating disk 31. This rotating disk 31 can be rotated around an axis 32 with respect to the base disk 30. The base disk 30 is connected via a corresponding connection 33 to the line 9 leading to the vacuum pump 8. In addition a corresponding borehole 34 crosses through the base disk 30, the borehole 34 having a borehole opening 35 in the direction of the rotating disk 31. In this case two boreholes 36 and 37 parallel to the axis pass through the rotating disk 31, the borehole 36 parallel to the axis having a connection to the line piece 11, whereas the borehole 37 parallel to the axis is connected to the tubing 26. Depending on the rotation of the rotating disk 31 either the borehole 36 parallel to the axis or the borehole 37 parallel to the axis is connected to the borehole 34. Consequently a connection is established either between the vacuum pump 8 and the chamber 13 or between the vacuum pump 8 and the collecting container 24. Thus, depending on the desired operating position, either tissue fluid is directed into the collecting container 24 or cutoff tissue samples are directed into a test tube 6.

Figure 5:
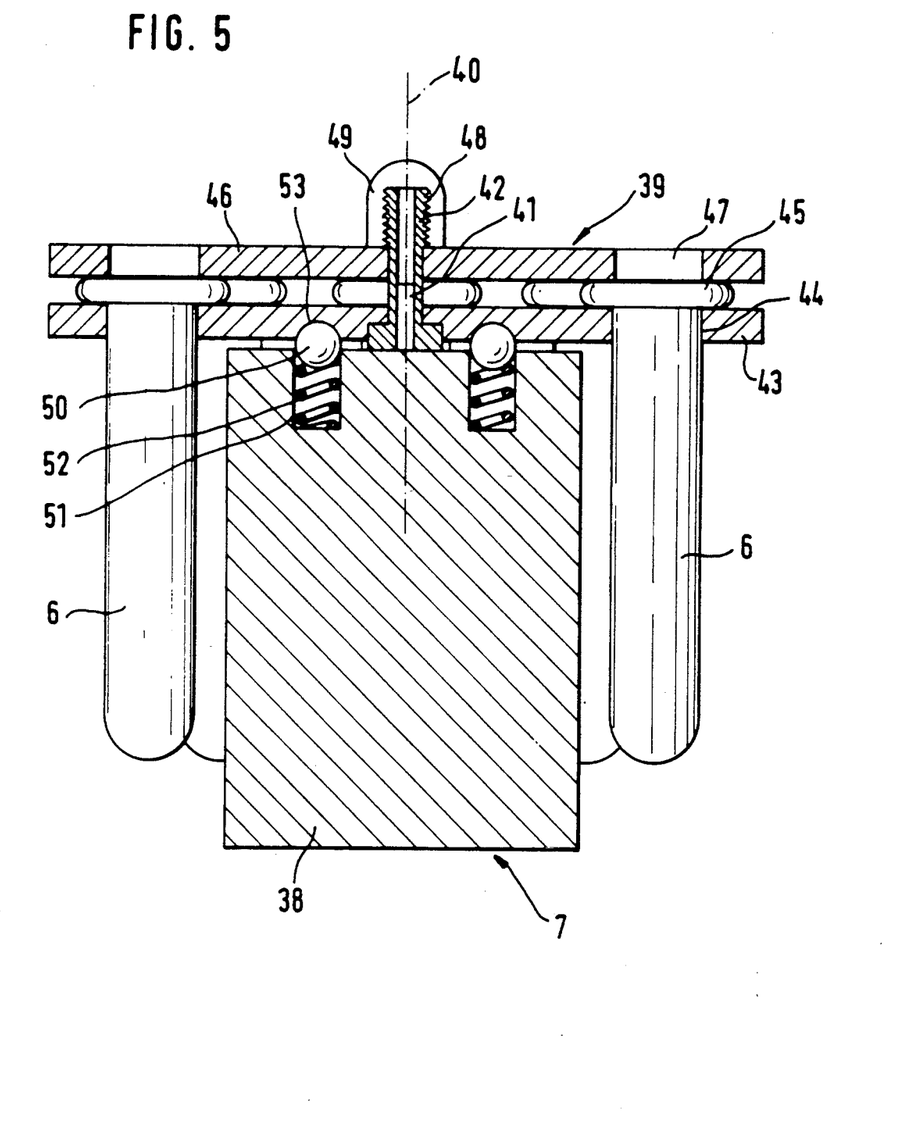
FIG. 5 shows an enlarged cross-section through a collecting apparatus of the device according to FIGS. 1 and 2.

According to FIG. 5 the collecting apparatus has a sealing body 38 (not shown for the sake of clarity) which optionally has a, for example, pneumatic drive for rotating plate 39. This rotating plate 39 in this case rotates around an axis of rotation 40, a corresponding drive shaft being merely indicated by 41. This drive shaft 41 engages as a pin in a connection sleeve 42, which in turn is connected to a supporting disk 43.

The supporting disk 43 has push-through openings 44 for test tubes 6, such test tubes 6 resting with their collar 45 on the supporting disk 43. Above this a corresponding covering disk 46 is provided, which in turn has corresponding openings 47 to the test tubes 6. In the operating position these openings 47 are surrounded by the ring seal 15.

The connection sleeve 42 similarly penetrates the covering disk 46 and, after penetration, has an outer thread 48. In the operating position a screw head 49 is placed on this outer thread 48, the screw head 49 serving to hold the rotating plate 39 together.

If, for example, all the test tubes 6 are to be filled, all that is required is for the complete rotating plate 39 to be pulled off the drive shaft 41 and replaced by a new one.

Corresponding locking balls 50, which rest in blind bores 51 of the supporting body 38 on helical springs 52, serve to align the test tubes 6 or the openings 47 with respect to the transmission head 4. On the other side these locking balls 50 engage in corresponding locking depressions 53 of the supporting disk 43. The rotating plate 39 is timed in this way. Other locking members or timing are also possible and are covered by the inventive idea. Such timing can take place both automatically and semiautomatically.

Figure 6:
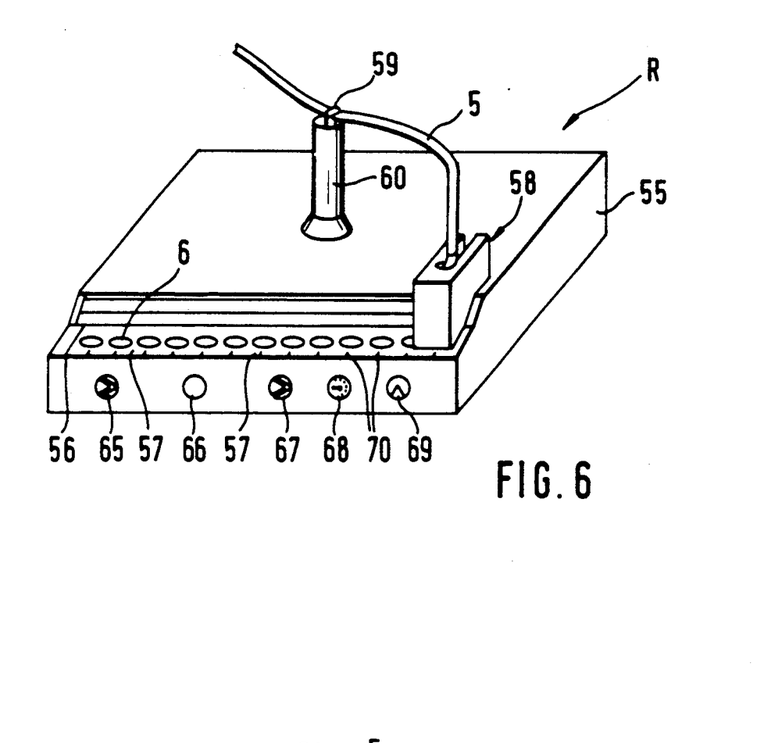
Figure 7:
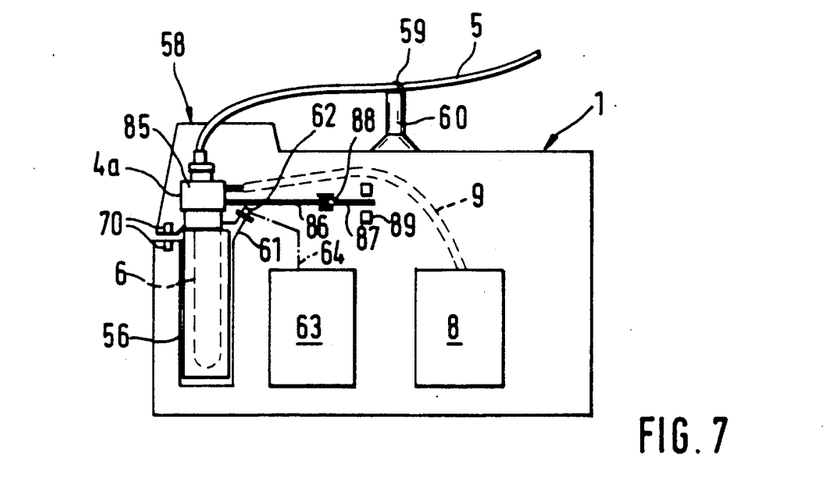
FIG. 7 shows a diagrammatically represented cross-section through a device according to the invention similar to FIG. 6.

FIGS. 6 and 7 represent an automatic device for the recovery of tissue samples, tissue fluid or similar.

For this purpose this device R exhibits a housing 55, which has, at the front, a shaft 56 or magazines 57 arranged in series to accommodate test tubes 6. Such magazines 57 may be passed over by a carriage 58, into which the transmission head 4 (see FIG. 7) is inserted. The tubing 5 leads from this transmission head 4 to the medical apparatus (not shown in greater detail) for cutting off a tissue sample. In the present exemplary embodiment this tubing 5 is held by a clamp 59 on a tubing support 60, which in turn rests on the housing 55.

The carriage 58 is moved along a guide rail 61 connected to the housing 55 and for this purpose said guide rail 61 is, for example, contacted on both sides by rollers 62.

The carriage 58 is driven by means of a transport motor 63, which is only indicated diagrammatically in FIG. 7. Similarly, the gear connection 64 between the transport motor 63 and the carriage 58 is only indicated diagrammatically by a dot-dash line.

In the exemplary embodiment 4a, shown in of the transmission head the vacuum line 9 leading from the vacuum pump 8 opens directly into the transmission head 4a itself. This transmission head 4a is described below in greater detail.

An on-off switch 65, a vacuum metering regulator 66, a transport switch 67, a test tube counter 68 and a switch 69 for filling, for example, a secretion bottle, are provided on the front side of the device R.

The movement of the carriage 58 or its stopping above a corresponding test tube 6 is controlled, for example, by sensors 70, which may be proximity switches or magnetic switches.

Figure 8:
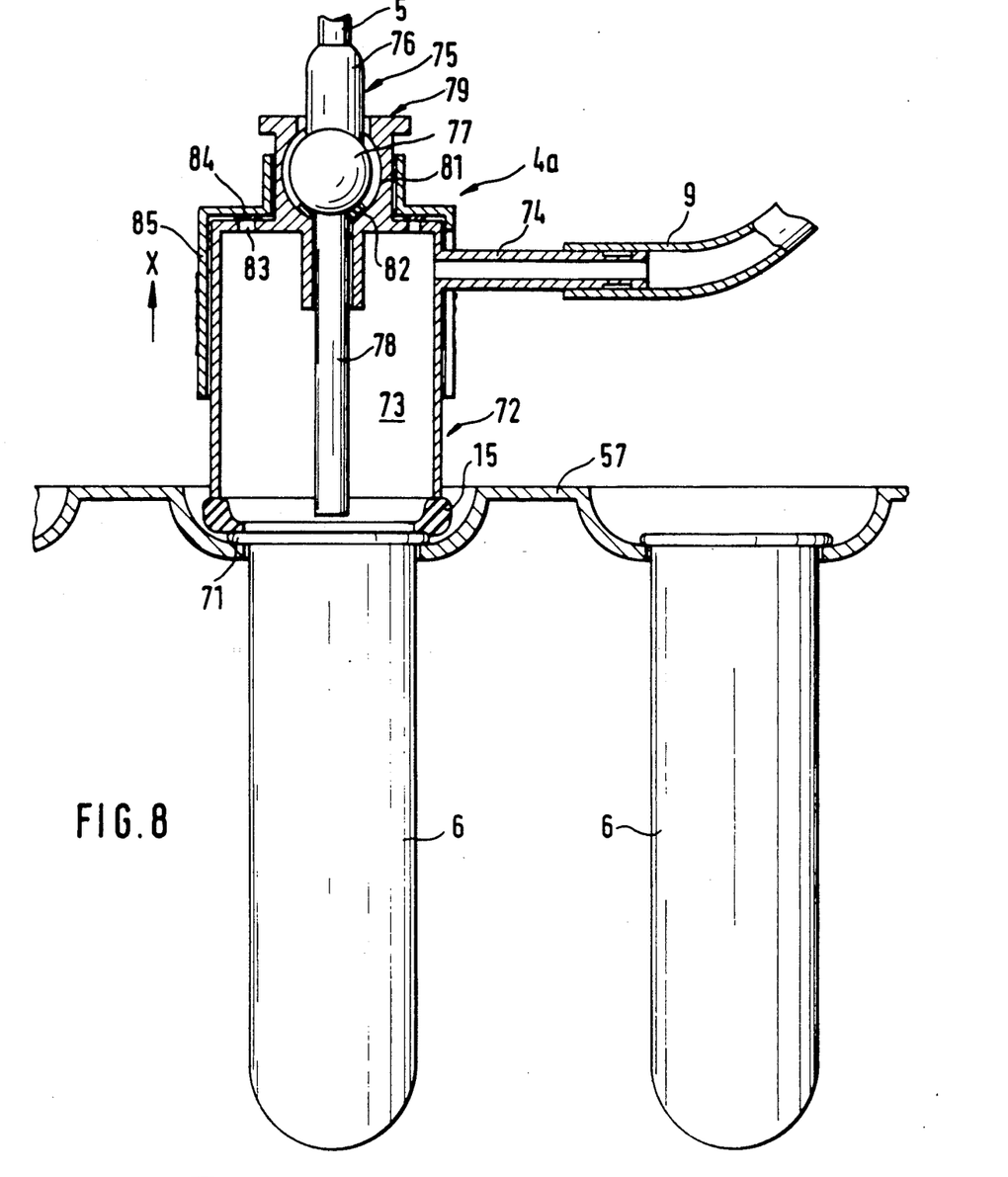
FIG. 8 shows an enlarged cross-section through a partial region of the invention according to FIGS. 6 and 7.

FIG. 8 shows in an enlarged view how the test tubes 6 are inserted into a magazine 57. A transmission head 4a is placed on the upper edge 71 of a test tube 6. The ring seal 15 provides sealing in the area of attachment.

The transmission head 4a has a principal housing 72, which surrounds an inner chamber 73. This inner chamber 73 is connected via a connection nozzle 74 to the vacuum line 9 and can thus be evacuated.

In the upper region a connection piece 75 for the tubing 5 is inserted into the principal housing 72. In this case the tubing 5 fits in an insertion piece 76, which is connected to a ball 77. From this ball 77 there then emerges a small tube 78, through which the extracted tissue sample drops into the test tube 6. It is self-evident that the connection piece 75 contains an axial passage through the insertion piece 76, the ball 77 and the small tube 78.

The connection between the connection piece 75 and the principal housing 72 is effected by inserting the ball 77 into a segmented ring sleeve 79.

Figure 9:
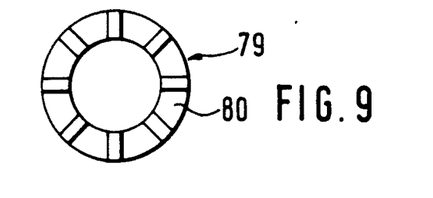
FIG. 9 shows a plan view of a part of a transmission head.

This segmented ring sleeve 79 consists, as shown in particular in FIG. 9, of individual segments 80 which can bend up outwards and thus allow the ball 77 to pass into a ball seat 81. The ball seat 81 also contains a seal 82, against which the ball 77 is pressed when a vacuum is created within the inner chamber 73.

Next to the ring sleeve 79 there are ventilation openings 83, comparable with the boreholes 29 in the principal housing 72. In the operating position these ventilation openings 83 are closed by a seal 84. This seal 84 is connected to a sliding sleeve 85, which surrounds the principal housing 72 at least partially. If this sliding sleeve 85 is displaced in the direction x the ventilation openings are also exposed and the chamber 73 can be ventilated.

In the automated embodiment of the invention according to FIGS. 6 and 7 this movement of the sliding sleeve 85 takes place automatically via a linkage 86 which is contacted by a movement arm 87. The corresponding rotation of the movement arm around an axis of rotation 88 is effected by an electromagnetic drive 89.

I claim:

1. A device for recovering a tissue sample comprising a surgical instrument for taking a tissue sample:
    tubing having one end connected to said surgical instrument and the other end connected to a transmission head provided with sealing means for sealing and seating said transmission head to a tissue collecting apparatus;
    a rotary lever connecting said transmission head to a rotary valve unit, said rotary lever having a borehole; and
    a hollow connecting piece having one end in communication with said borehole and the other end in communication with a vacuum-producing means such that when said transmissions head is seated on said collecting apparatus as vacuum-producing means draws air from said hollow connecting piece, said borehole, said transmission head and said tubing for drawing a tissue sample from said surgical instrument, through said tubing, to said transmission head from which said sample is deposited into said collecting apparatus.

2. The device according to claim 1 characterized in that said connecting piece is permanently connected to said borehole and selectively connected to said vacuum-producing means.

3. The device according to claim 1 wherein the communication between the transmission head and the vacuum-producing means can be selectively established and broken with the rotary valve unit.

4. The device according to claim 3 wherein the rotary valve unit consists of a base disk (30) and a rotating disk having said connecting piece.

5. The device according to claim 4 wherein the base disk has a first path for communicating said connecting piece to the vacuum-producing means.

6. The device according to claim 5 wherein the rotating disk has a second borehole which can be connected alternatingly with the first path or a second path provided in the base disk.

7. The device according to claim 6 wherein the second borehole is connected to a conduit to a tissue fluid collecting container.

8. The device according to claim 7 wherein the collecting container is selectively connected by tubing means (22) to the transmission head.

9. The device according to claim 8 wherein the longitudinal borehole is connected on one side with the connection piece and on the other side opens into a chamber formed in the transmission head.

10. The device according to claim 9 wherein the chamber is penetrated partially by a sleeve which is connected to the tubing.

11. The device according to claim 10 wherein the sleeve can be selectively placed onto the tubing means.

12. The device according to claim 11 wherein the chamber is provided with ventilating means.

13. The device according to claim 12 wherein the ventilation means comprises a borehole for ventilating the chamber which is selectively covered by a sliding sleeve having a seal.

14. The device according to claim 1 wherein the transmission head consists of a principal housing surrounding an inner chamber (73) into which a connection nozzle for the vacuum-producing means opens.

15. The device according to claim 14 wherein the tubing opens into a connection piece which engages in a locking manner with the transmission head.

16. The device according to claim 15 wherein a segmented ring sleeve is molded onto the transmission head into which ring sleeve a ball on the connection piece (75) can be inserted.

17. The device according to claim 16 wherein the ball is supported via a seal against the ring sleeve.

18. The device according to claim 1 wherein the collecting apparatus consists of a supporting body and a rotating plate placed thereon.

19. The device according to claim 18 wherein drive means for rotating the plate around an axis of rotation is provided on the supporting body.

20. The device according to claim 19 wherein spring-mounted locking balls are provided between the rotating plate and the supporting body (38) in order to determine the position of the rotating plate (39).

21. The device according to claim 19 wherein the rotating plate consists of a supporting plate and a covering disk between which collars of test tubes are held.

22. The device according to claim 20 wherein the rotating plate is placed releasably on the supporting body.

23. The device according to claim 1 wherein the transmission head is arranged on a carriage which is moved by means of a drive along a guide rail.

* * * * *